United States Patent [19]
Campbell et al.

[11] Patent Number: 5,843,703
[45] Date of Patent: Dec. 1, 1998

[54] ENHANCED PRODUCTION OF TOXIC POLYPEPTIDES IN PROKARYOTES

[75] Inventors: Judith L. Campbell, Sierra Madre; William C. Brown, Pasadena, both of Calif.

[73] Assignee: California Institute of Technology, Pasadena, Calif.

[21] Appl. No.: 296,087

[22] Filed: Aug. 25, 1994

Related U.S. Application Data

[63] Continuation of Ser. No. 7,590, Jan. 22, 1993, abandoned.
[51] Int. Cl.$^6$ .............................. C12N 15/00; C12N 7/00; C12N 1/20; C12P 21/00
[52] U.S. Cl. .................. 435/69.1; 435/172.1; 435/235.1; 435/236; 435/252.3; 435/252.8; 435/320.1; 435/375; 536/23.1; 536/23.72
[58] Field of Search ................................ 435/69.1, 172.3, 435/320.1, 236, 252.3, 235.1, 252.8, 370.2, 375; 536/23.72, 23.1; 535/38, 73

[56] References Cited

U.S. PATENT DOCUMENTS

| | | | |
|---|---|---|---|
| 4,952,496 | 8/1990 | Studier et al. | 435/91.41 |
| 5,064,757 | 11/1991 | Simon et al. | 435/71.2 |

OTHER PUBLICATIONS

Michalewicz, J. et al. 1992. *Virology* vol. 186 p. 452–462.
Dunn, J.J. et al. 1981. *J. Mol. Biol.* vol. 148 p. 303–330.
Hesselbach, B.A. et al. 1977. *J. Virol.* vol. 24 p. 736–745.
L.D. Simon et al., Bacteriophages inhibit degradation of abnormal proteins in *E. Coli. Nature* 275:424–428 (1978).
L.D. Simon et al., Stabilization of proteins by a bacteriophage T4 gene cloned in *Escherichia coli. Proc. Natl. Acad. Sci. USA* 80:2059–2062 (1983).

B.S. Singer et al., Phage T4 expression vector: protection from proteolysis. *Gene* 106:1–6 (1991).

R. Hausmann et al., Inhibition of gene expression of T7–related phages by prophage P1. *Mol. Gen. Genet.* 212:543–547 (1988).

J. Heitman et al., Phage Trojan horses: a conditional expression system for lethal genes. *Gene* 85:193–197 (1989).

B.A. Moffat et al., Entry of bacteriophage T7 DNA into the cell and escape from host restriction. *J. Bacteriol.* 170:2095–2105 (1988).

C. Olenik et al., T7 infection–dependent selective expression of cloned genes in P1–lysogenic *Escherichia coli. Biochem. Biophys. Res. Commun.* 179:1200–1204 (1991).

W.C. Brown et al., Cloning and overexpression of yeast DNA polymerase δ in *E. coli. J. Cell. Biochem.* Supplement 16 B, p. 104, Jan. 5–Feb. 8 (1992).

*Primary Examiner*—George C. Elliot
*Assistant Examiner*—Sean M'Garry
*Attorney, Agent, or Firm*—Flehr Hohbach Test Albritton & Herbert LLP

[57] ABSTRACT

Compositions for enhancing the production of toxic polypeptides in prokaryotic hosts comprise a coding nucleic acid and a bacteriophage nucleic acid. The coding nucleic acid encodes a promoter operably linked to a gene encoding a selected toxic protein. The bacteriophage nucleic acid contains at least one gene from the early region of a T7-like bacteriophage other than an RNA polymerase. When both the coding nucleic acid and the bacteriophage nucleic acid are used to transform or transfect a prokaryotic host, the production of the toxic polypeptide is greater than the level of production of the same toxic polypeptide when the same host is transformed only with the coding nucleic acid.

37 Claims, 7 Drawing Sheets

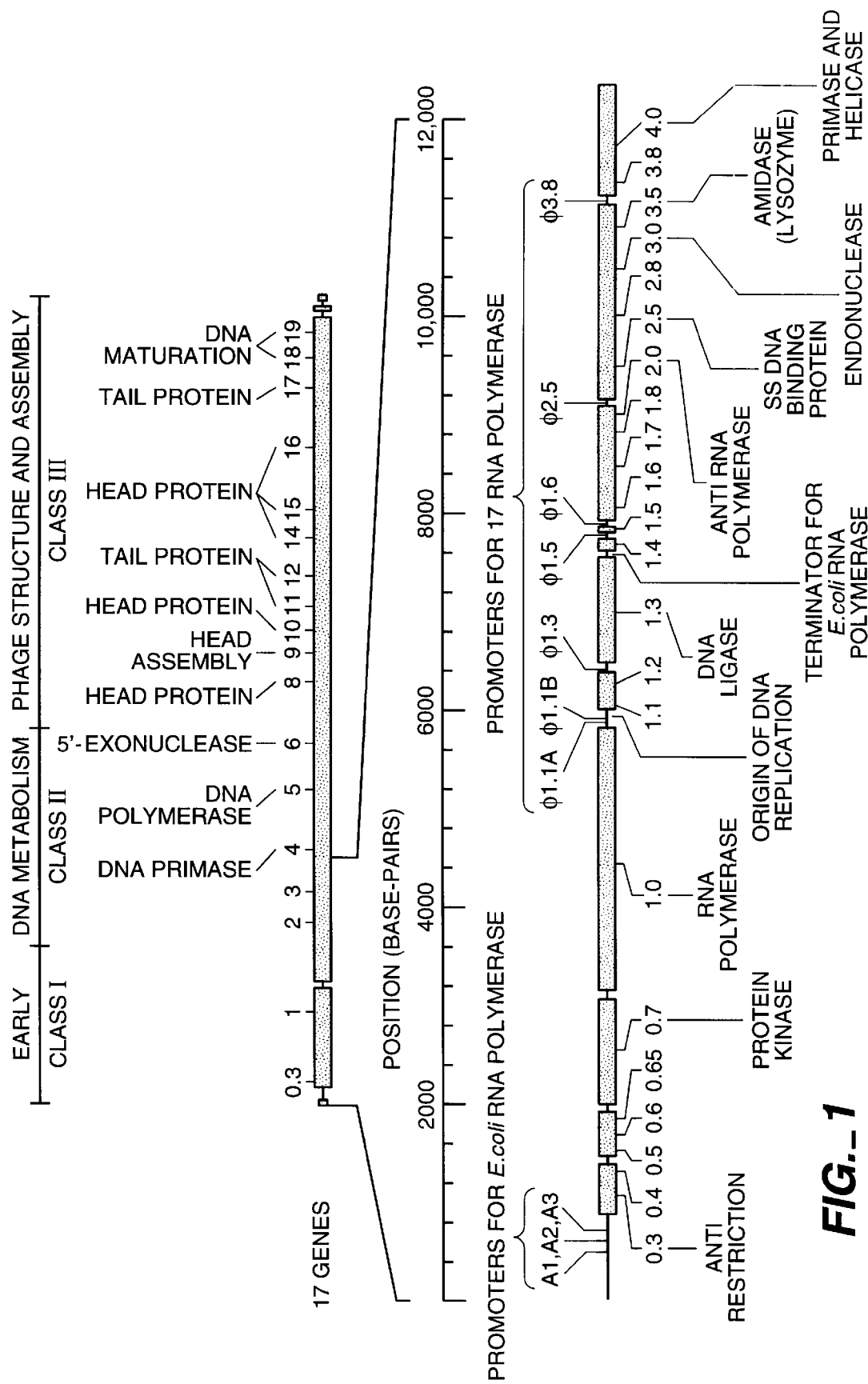
FIG._1

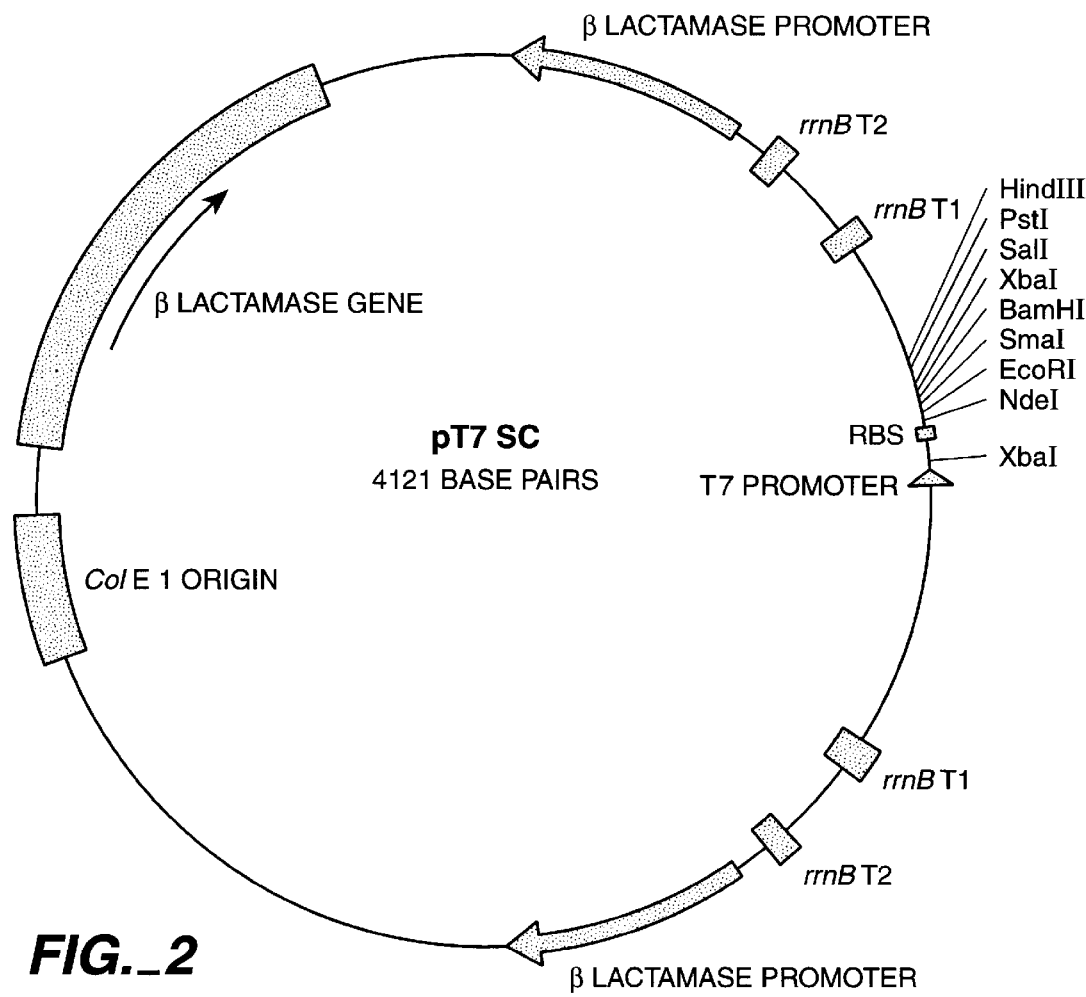
FIG._2

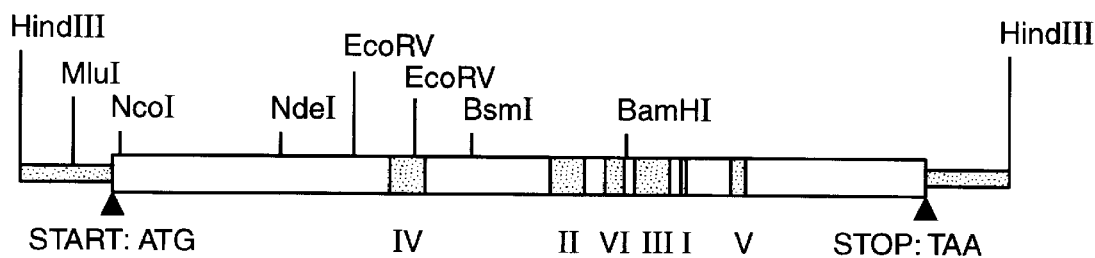
FIG._3A CONSERVED REGIONS
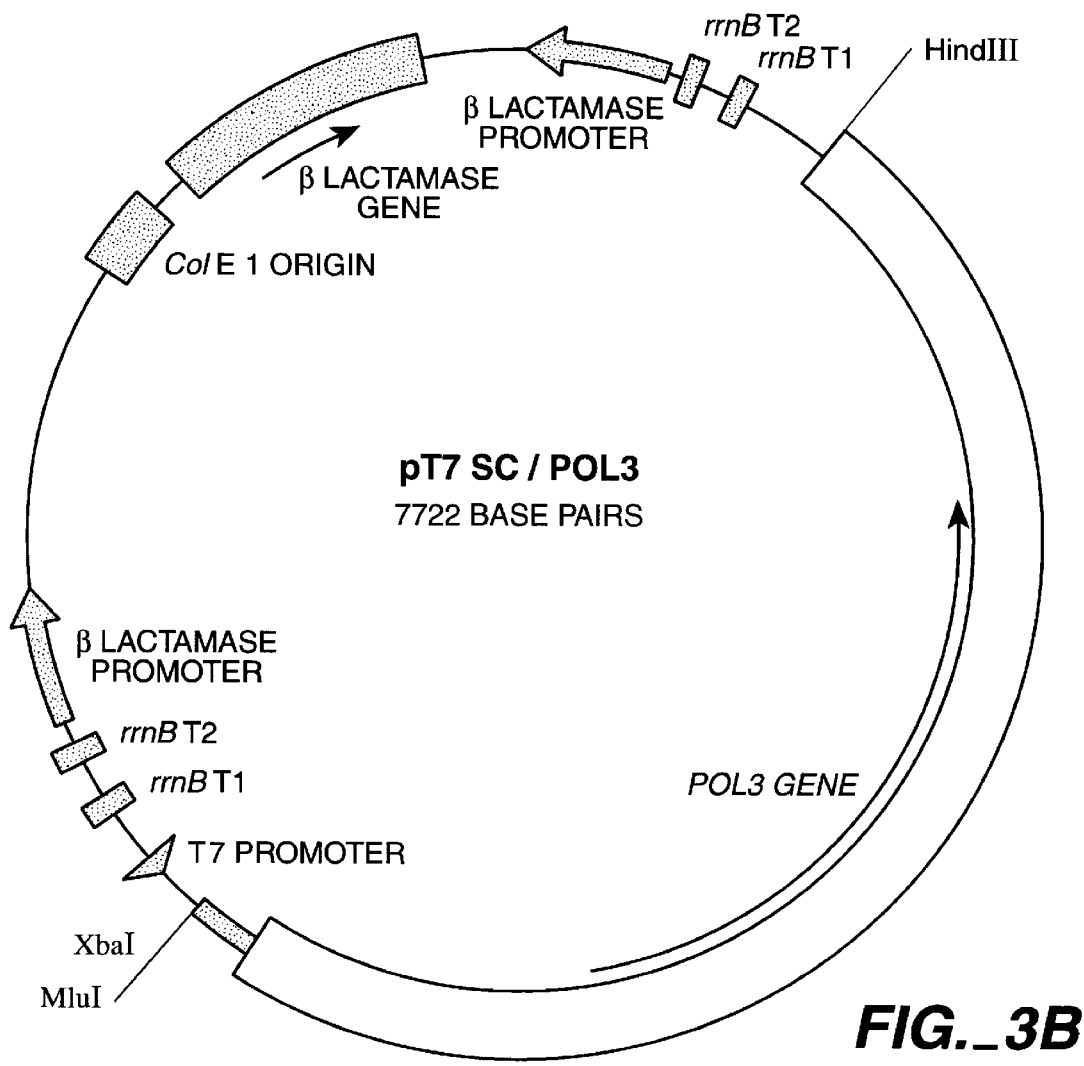
FIG._3B

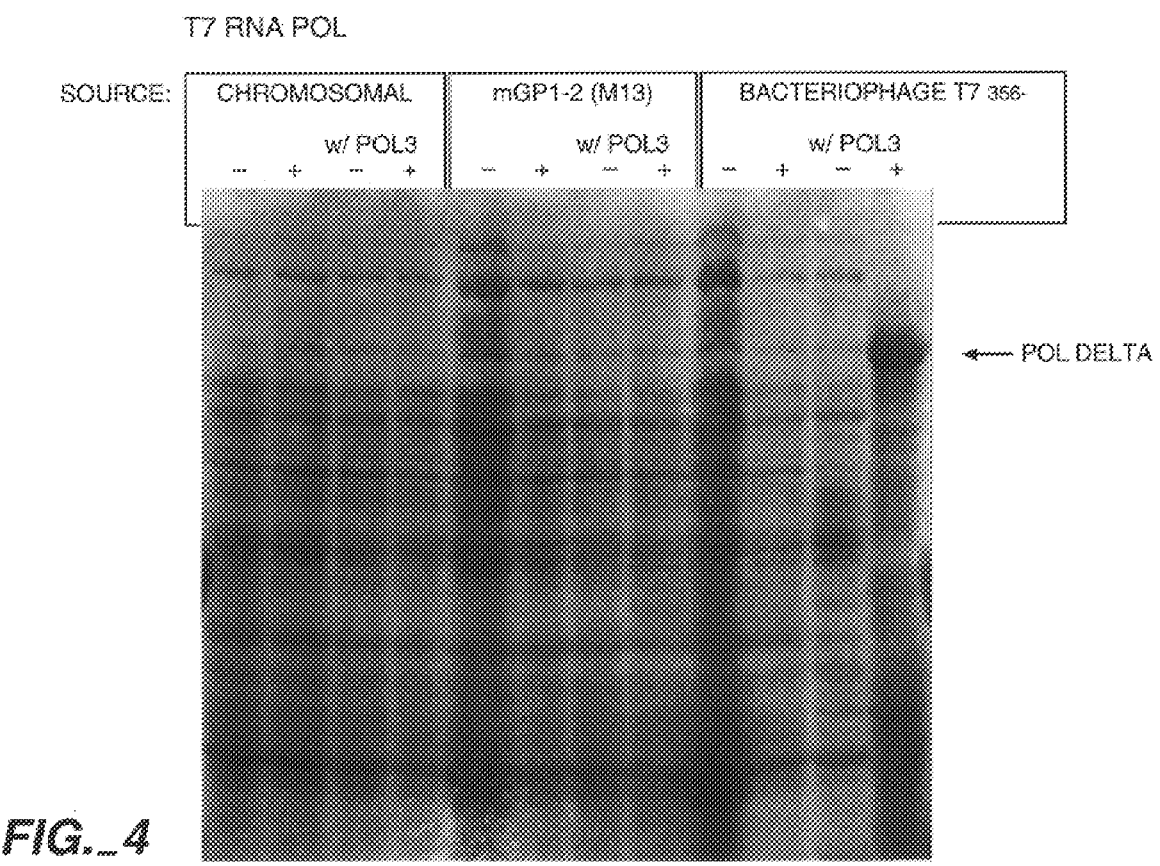
FIG._4

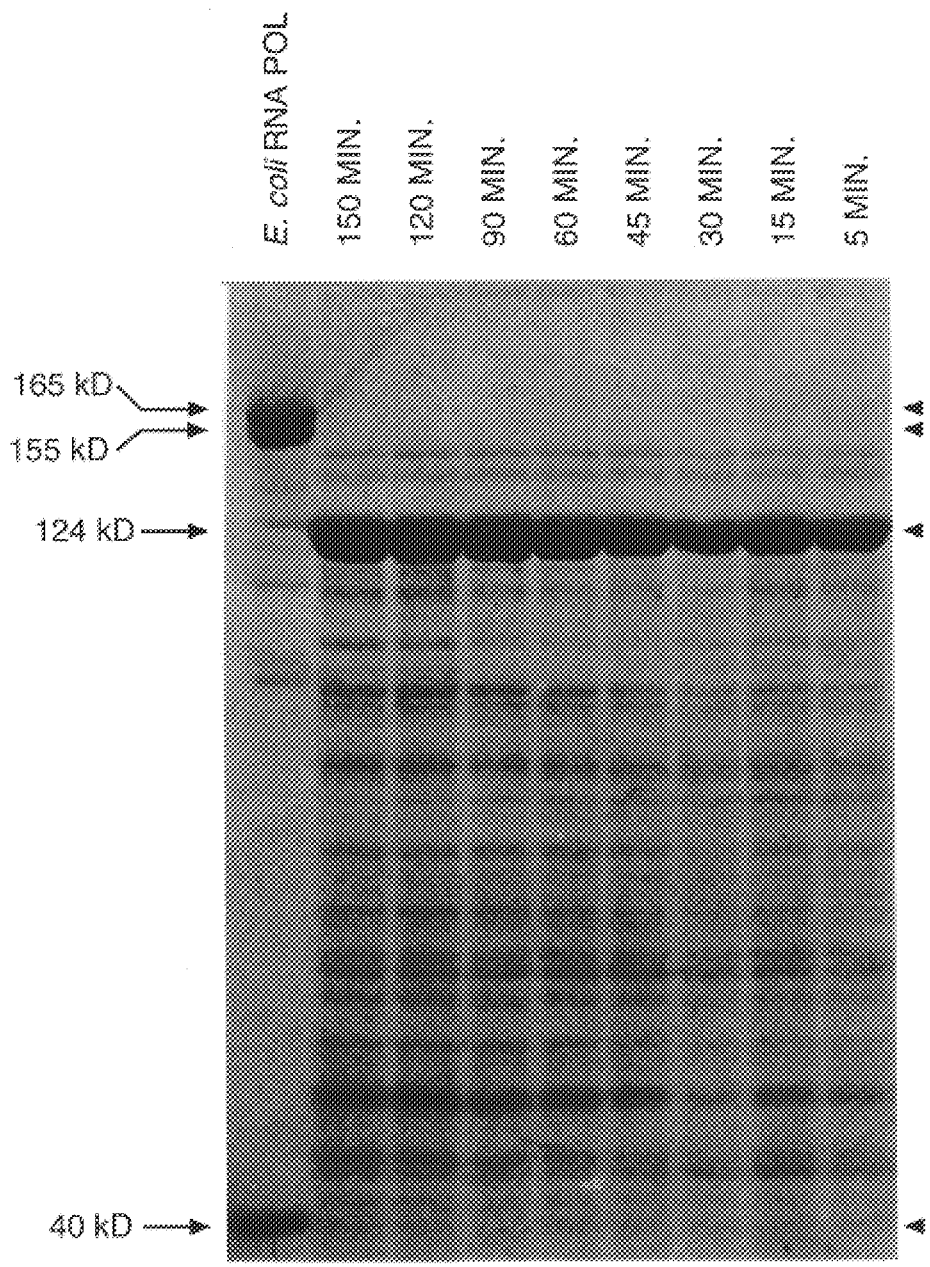
FIG._5

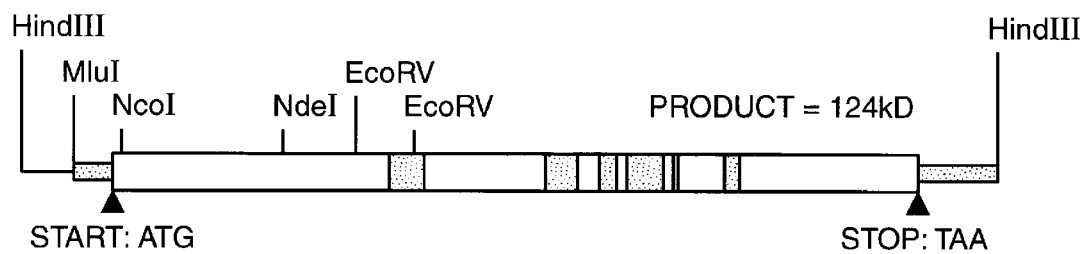
FIG._6A
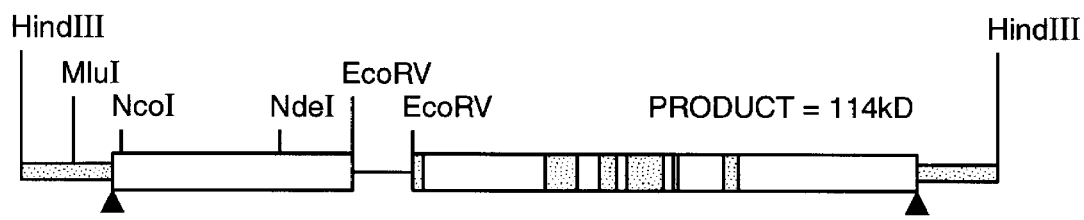
FIG._6B
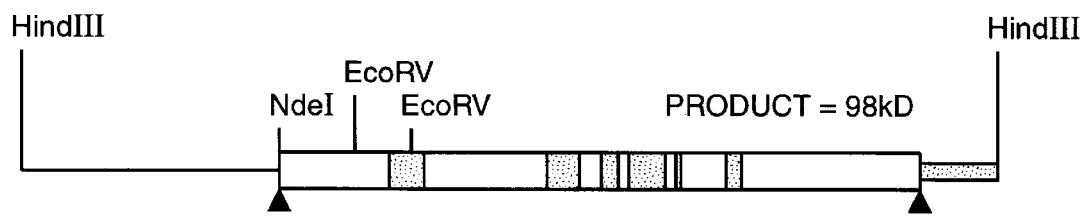
FIG._6C
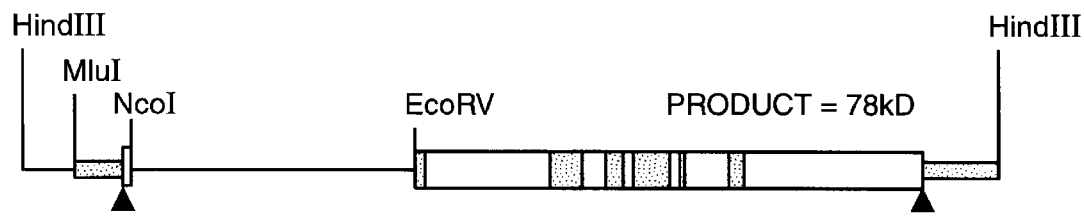
FIG._6D

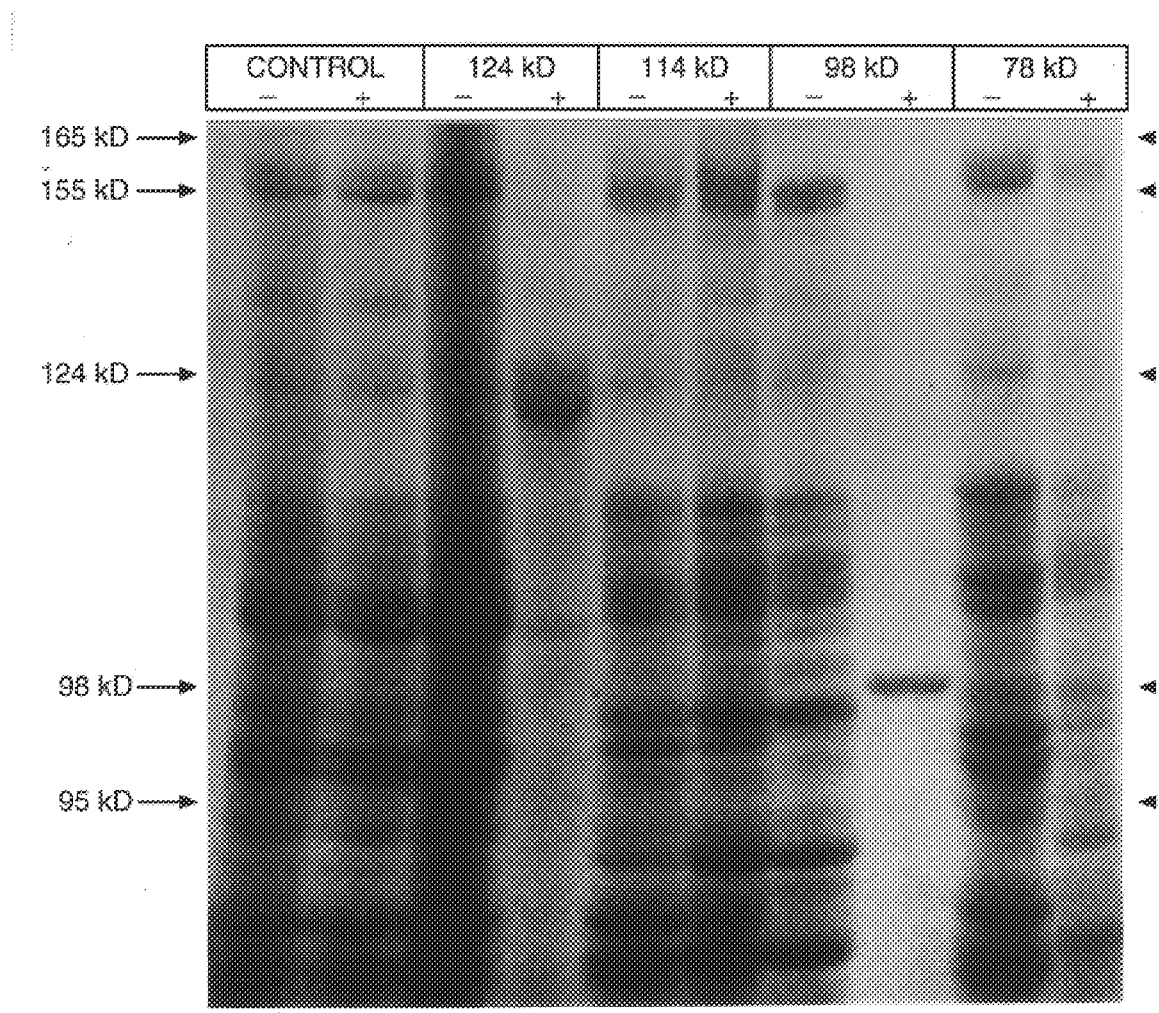
FIG._7

ENHANCED PRODUCTION OF TOXIC POLYPEPTIDES IN PROKARYOTES

This is a continuation of application Ser. No. 08/007,590 filed Jan. 22, 1993, and now abandoned.

The U.S. Government has certain rights in this invention pursuant to Contract No. USPHS 25508 and NIH NRSA CA08692 awarded by the National Institute of Health.

TECHNICAL FIELD OF THE INVENTION

The invention relates to compositions which include nucleic acid derived from T7-like bacteriophage to enhance the production of toxic polypeptides by prokaryotic host cells.

BACKGROUND OF THE INVENTION

Prokaryotic cells are the system of choice for expression of cloned genes encoding useful eukaryotic and prokaryotic polypeptides, in part, because of the low cost and ease of maintaining cultures of such cells. Very few failures have been encountered when the genes used for transformation are from *Escherichia coli* or other prokaryotic organisms. However, as more and more eukaryotic genes have been cloned and characterized, a problem has arisen in their expression in bacteria. Often the gene is toxic, as evidenced by the instability of the plasmid containing the gene.

Many foreign polypeptides are unstable in prokaryotic cells because of their degradation by the host's proteolytic enzymes. In one approach to this problem, host cells have been transformed with a plasmid containing an insert of the T4 pin gene (U.S. Pat. No. 5,064,757 and Simon et al., *Proc. Natl. Acad. Sci. USA* (1983) 80:2059–2062). Another related method utilizes infection of *E. coli* with bacteriophage T4 (Singer et al., *Gene* (1991) 106:1–6). These approaches, however, result in only limited inhibition of proteolysis.

In yet another approach, expression vectors that rely on a bacteriophage T7 promoter have been developed. A bacteriophage T7 promoter, which is not recognized by the RNA polymerase of *E. coli*, is used to regulate expression of the gene (Tabor and Richardson (1985) *Proc. Natl. Acad. Sci. U.S.A.*, 162:1074–1078; Studier and Moffat (1986) J. Mol. Biol., 189:113–130). The T7 RNA polymerase is delivered to the system on another plasmid under the control of a thermolabile lambda repressor and induced by temporarily raising the temperature (Tabor and Richardson (1985) *Proc. Natl. Acad. Sci. U.S.A.*, 162:1074–1078). Because repression is not complete, foreign genes often are not stable even in these cells.

Another method for the introduction of T7 RNA polymerase uses a lambda lysogen cell line in which the T7 RNA polymerase gene is under the control of the IPTG-inducible lac promoter. In an attempt to mitigate the effects of RNA polymerase gene expression, a plasmid containing the gene for T7 lysozyme has been used (Studier and Moffat (1986) *J. Mol. Biol.* 189:113–130). T7 lysozyme is capable of cleaving and inactivating T7 RNA polymerase. When IPTG is added, the cell is induced to produce much higher levels of T7 RNA polymerase.

Yet another method of introducing T7 RNA polymerase consists of infecting the cells containing the gene of interest with an M13 phage that carries the T7 RNA polymerase gene, also under lac control, and inducing with IPTG. These latter systems have not been effective in overexpressing eukaryotic genes in bacteria. Often the yield of protein is quite low, if the protein is produced at all. The general problems associated with expressing eukaryotic genes in *E. coli* are detailed in Gene Cloning, An Introduction, 2nd edition, by T. A. Brown (1990) Chapman and Hall, publishers, London.

Abortive infection of *E. coli* (P1) (lysogenic for phage P1) with phage T7 has also been used as a means to provide T7 RNA polymerase. The expression of the gene under the control of the T7 promoter is attributed to the production of T7 RNA polymerase which is known to be synthesized during T7 infection of P1 lysogens. Bacterial growth is not quantitatively impaired by the introduction of T7 to these cultures. Olenik, et al. (1991) *Biochem. Biophys. Res. Comm.*, 179:1200–1204. The phage T7 gene 0.3 protein product is known to bind and inactivate host restriction enzymes that would normally degrade T7 DNA which is how the phage establishes infection. However, this T7 protein does not inhibit the P1 encoded restriction endonuclease EcoP1 which digests the T7 DNA before transcription of the early genes has been completed. Moffat and Studier (1988) *J. Bact.* 170:2095–2105.

Finally, one author has asserted that T4, T5 and T7 inhibit degradation of puromycyl protein fragments in *E. coli*. Simon, et al. (1978) *Nature*, 275:424–428. However, the only known example utilizing this system with polypeptides heterologous to the *E. coli* host involve the use of a T4 DNA fragment in conjunction with the expression of human fibroblast interferon. See U.S. Pat. No. 5,064,757.

Although the use of eukaryotic cells, such as CHO cells may obviate the problem of low yield from eukaryotic genes, such cell cultures are far more expensive and difficult to maintain than cultures of prokaryotic cells.

A need therefore exists for prokaryotic expression systems which are capable of expressing those foreign (heterologous) genes which otherwise do not produce satisfactory amounts of the foreign gene product.

Accordingly, it is an object of the invention to provide novel nucleic acid compositions, prokaryotic host cells transformed with such nucleic acid compositions and methods for making such host cells to enhance the production of foreign polypeptides by genes which are otherwise toxic or unstable in such bacterial hosts.

SUMMARY OF THE INVENTION

The invention includes compositions comprising a coding nucleic acid and a bacteriophage nucleic acid. The coding nucleic acid encodes a promoter operably linked to a gene encoding a selected toxic protein. The bacteriophage nucleic acid contains at least one gene from the early region of a T7-like bacteriophage other than an RNA polymerase. When both the coding nucleic acid and the bacteriophage nucleic acid are used to transform a prokaryotic host, the production of the toxic polypeptide is greater than the level of production of the same toxic polypeptide when the same host is transformed only with the coding nucleic acid.

The invention also includes a method for enhancing production of toxic polypeptides in prokaryotic hosts. The method comprises transforming a prokaryotic host with the aforementioned nucleic acid composition and subjecting the host to conditions which permit the expression of the coding nucleic acid.

The invention also includes prokaryotic hosts transformed with the aforementioned nucleic acid composition.

BRIEF DESCRIPTION OF THE DRAWINGS

FIG. 1 depicts the genomic map of bacteriophage T7 with a detailed view of the first third of the genome (from Molecular Biology of the Gene, Watson et al., (1976) The Benjamin/Cummings Publishing Company, 4th ed., 1987, p. 512).

FIG. 2 shows plasmid pT7SC.

FIG. 3A shows a linear map of the *Saccharomyces cerevisiae* POL3 gene. The open reading frame is shown as a thick white box, non-coding sequences are medium thickness and shaded. The black boxes in the coding region correspond to the conserved regions associated with α-like DNA polymerases (Wong et al (1988) *EMBO J.* 7:37–47).

FIG. 3B shows the pT7 SC/POL3 vector used for expression of the POL3 gene.

FIG. 4 shows the dependence of expression of POL3 on infection by mutant bacteriophage T7.

FIG. 5 is a time course of POL3 expression.

FIGS. 6A–6D show deletion and truncation constructs of POL3. The thin lines represent removed sequences, medium shaded boxes are non-coding regions and the large white boxes are the open reading frames with the six conserved regions in black. The full-length construct is shown in FIG. 6A as it appears in pT7SC/POL3. Truncated constructs are shown in FIGS. 6B, 6C and 6D.

FIG. 7 shows expression of various forms of POL3 by infection with bacteriophage $T7_{356}$. Cell lines contained the constructs indicated by molecular weight and were either infected (+) or uninfected (−).

DETAILED DESCRIPTION OF THE PREFERRED EMBODIMENTS

The invention is based, in part, upon the enhanced production of the product of an otherwise toxic gene (in this case, Saccharomyces cerevisiae DNA polymerase δ) observed in the prokaryotic *Escherichia coli* when the host was transformed with a mutant T7-like bacteriophage (in this case, a mutant T7). This mutant bacteriophage was capable of expressing early region genes but the mutations prevented the phage from completing its life cycle. When the mutant bacteriophage is not used, the product of the toxic gene was not detected.

As used herein, the term "prokaryotic host" herein refers to enterobacterial and non-enterobacterial strains. Examples of enterobacterial strains include, but are not limited to, *Escherichia coli, Serratia marcescens, Salmonella typhimurium,* Citrobacter spp. Ci23 and Klebsiella spp. 390. Non-enterobacterial strains include, but are not limited to, *Pseudomonas putida* and *Caulobacter crescentus.* A particularly preferred host is *E. coli.*

As used herein, the term "toxic gene" refers to a gene which leads to plasmid instability. Instability can be attributable either to DNA sequence or to protein product effects. These may be distinguished by the ability of a very tightly regulated plasmid to carry a gene encoding a toxic polypeptide, as in the case of DNA polymerase δ, while instability due to a sequence effect would not be stabilized by suppressing inappropriate transcription. Therefore, a toxic gene is defined as one encoding a toxic polypeptide. When incorporated into a prokaryotic host, the levels of production of this protein are often substantially reduced or undetectable. In many instances, toxic genes comprise heterologous eukaryotic genes which encode important proteinaceous molecules such as POL3 (Simon, et al. (1991) *EMBO J.* 10:2165–2170) and HSP60 (Smiley, et al. (1992) *Nuc. Acids Res.* 20:4913–4918). However, heterologous genes other than eukaryotic genes can also be toxic genes. For example, T4 regA (Miller, et al. (1987) *J. Mol. Biol.* 194:397–410) and T7 gene 2 (Tabor, et al. (1985) *Proc. Natl. Acad. Sci. USA* 82:1074–1078) exhibit instability and/or reduced production levels of the gene product when transformed in a prokaryotic host. Thus, a toxic gene is any gene which is either unstable in the prokaryotic host, i.e., is incapable of being maintained extra-chromosomally, or which results in the production of the gene product at levels which are either not detectable or which are lower than would otherwise be expected. Again, toxicity initially manifests itself through plasmid instability. If the plasmid can be stabilized by suppressing transcription, it can be assumed that the protein product is toxic. Low yield upon induction may then be attributed to protein toxicity rather than some other cause. Non-toxic proteins may also be produced in low yield for a variety of reasons, such as codon usage, and this system may also be helpful for these proteins as well by reducing competition at the ribosome during translation. Although the skilled artisan will readily be able to determine which genes are toxic, one measure of whether a gene is toxic is to determine the expression level of a gene endogenous to the prokaryotic host and compare that level of expression directly to the expression of the putative toxic gene operably linked to the promoter from the endogenous gene. If the level of production of gene product per gene copy is less than that observed for the endogenous gene (or that observed when the same promoter is operably linked to a different endogenous gene), the gene of interest is considered to be a toxic gene. In general, the level of production of toxic gene product will be less than 50% of that otherwise expected and can be as low as 0%.

It is not known why some proteins are toxic while others are not. For some, there are functions which alter the normal regulatory processes of the cell such as transcription or translation but others have no defined effect. It is not clear why a protein such as DNA polymerase δ is not tolerated by the cell. It is possible that this protein binds to required bacterial proteins thus disrupting an essential function.

As used herein, a "coding nucleic acid" refers to a promoter operably linked to a nucleic acid coding for a toxic polypeptide. The promoter can be a promoter functionally recognized by the endogenous RNA polymerase of the prokaryotic host but is preferably a promoter which is recognized only by an RNA polymerase not found in the prokaryotic host. When a promoter is used which is recognized by the endogenous RNA polymerase, it is preferred that the promoter be from an inducible gene such as the IPTG-inducible lac promoter. In the preferred embodiments, however, the promoter is preferably recognized only by a non-endogenous RNA polymerase. Examples include T7-like bacteriophage promoters such as those from T7 genes which recognize T7 RNA polymerase as set forth in FIG. 1. When such non-endogenous promoters are used, it is necessary that the expression system include a source of an RNA polymerase which recognizes such promoters. When a bacteriophage promoter is used, it is preferred that the RNA polymerase be derived from the same bacteriophage, e.g., a T7 promoter used in conjunction with T7 RNA polymerase. However, this relationship is not necessary. All that is required is the presence of an RNA polymerase which functionally recognizes the promoter used.

It is preferred that other expression control sequences be included in the coding nucleic acid to maintain stringent control of expression of the toxic gene. In this regard, transcription terminators such as the rho-independent transcription terminators T1 and T2 from the rrnB operon of *E. coli* are positioned upstream and downstream from the coding nucleic acid so as to minimize read-through of spurious transcription into the coding nucleic acid. There are a number of other known termination sequences. However, the rrnB operon contains the only identified doublet of termination sequences and for this reason is considered the tightest transcription control sequence.

The term "T7-like bacteriophage" refers to any bacteriophage that is a phylogenetic relative of T7 bacteriophage. This term has a functional definition and includes such phages, classified as Podoviridae, that follow the T7 bacteriophage strategy of infecting prokaryotic cells based on selective transcription of a portion of the bacteriophage genome by a phage-coded RNA polymerase (Hausmann (1988), in "The Bacteriophages" Vol. 1, Editor: R. Calendar, Plenum Press, New York and London). Examples of T7-like bacteriophages include T1, T3, T7, ΦI, ΦII, BA14, A16, Φ1.2, K11, SP6, gh-1 and ΦCd1. A preferred bacteriophage is T7.

As used herein, a "bacteriophage nucleic acid" refers to a nucleic acid derived from a T7-like bacteriophage genome. The bacteriophage nucleic acid contains at least one gene other than the RNA polymerase of the early region of a T7-like bacteriophage nucleic acid. An example of such a bacteriophage nucleic acid is the mutant T7 bacteriophage used in the examples. This bacteriophage contains amber mutations in genes 3, 5 and 6. Genes 3 and 6 encode endo- and exo-nucleases which degrade the host DNA during infection. These genes are essential for replication since T7 is dependent on large pools of nucleotide precursors generated by the degradation of the host DNA by the genes 3 and 6 proteins. Thus, both of these genes are essential for the completion of the T7 life cycle. Further, gene 5 encodes the catalytic subunit of T7 DNA polymerase which is essential for replicating the phage genome. The mutations in genes 3, 5 and 6 therefore prevent the bacteriophage from completing its life cycle. When a T7-like bacteriophage is used, one or more of such mutations are required to prevent premature lysis of the host prokaryote. Such a mutant bacteriophage, however, meets the requirement of a bacteriophage nucleic acid in that it contains at least one gene, other than the bacteriophage RNA polymerase, within an early region of the T7-like bacteriophage.

The genome of a T7-like bacteriophage can be classified according to the time of expression and/or function of the gene products in the phage life cycle. FIG. 1 sets forth three gene classes for the T7 genome. Class I includes those genes which express "early proteins." Such genes generally utilize promoters which are recognized by the RNA polymerase of the normal infection host for the bacteriophage, e.g., E. coli RNA polymerase. Class II encode "early late proteins" and Class III genes encode "late proteins" which are involved in DNA metabolism and phage structure and assembly, respectively. The Class II and Class III genes generally utilize promoters which are specific for the T7 RNA polymerase encoded by gene 1.

In its broadest scope, the term "early region" of a T7-like bacteriophage includes Class I genes which encode the early proteins and all or part of the Class II genes. In the case of T7, this comprises approximately 45% of the T7 genome. One or more genes in the early region other than gene 1, which encodes the RNA polymerase, are responsible for the enhanced expression of toxic polypeptides as demonstrated in the examples. Candidates include gene 0.7 which encodes a protein kinase and gene 2 which is known to be an inhibitor of E. coli RNA polymerase. Thus, a preferred bacteriophage nucleic acid comprises an early region of the T7 bacteriophage extending from and including at least gene 0.3 through gene 2.0, with or without gene 1 encoding the phage RNA polymerase. Other preferred nucleic acids include the 0.7 and 2.0 genes of T7 alone or in combination.

In the preferred embodiments, one or more early region genes, other than the T7 RNA polymerase, are used as the bacteriophage nucleic acid to enhance production of the toxic polypeptide encoded by the coding nucleic acid. The determination of which of the one or more genes within the early region can be used for such purposes can be readily determined by the following protocol. Since the entire sequence of T7 DNA is available, the individual genes from the early region are cloned individually or in selected combinations by sing the polymerase chain reaction (PCR). Dunn and Studier (1983) J. Mol. Biol. 166:477–535. This technique is used to amplify the coding sequences of interest and then these sequences are cloned into a low copy number plasmid (such as pACYC 184) compatible with the expression vector (pT7SC) described. One assay for enhanced production of toxic polypeptide uses of strains transformed by these plasmids to produce, for example, yeast DNA polymerase δ. In this way, the individual genes or combination of genes required for enhanced production of toxic polypeptides are identified.

The coding nucleic acid and bacteriophage nucleic acid can be on separate plasmids or on the same plasmid used to transform the prokaryotic host. When a T7-like bacteriophage promoter is used in the coding nucleic acid, the RNA polymerase which recognizes such promoters may be maintained on the same plasmid, incorporated into the bacteriophage nucleic acid, incorporated into the chromosome of the host prokaryote or introduced by way of an infectious agent. When contained on the same plasmid or incorporated into the bacteriophage nucleic acid, the expression of the RNA polymerase is preferably under control of the heat-inducible λ promoter. To incorporate the RNA polymerase into the chromosome of the host prokaryot, a λ lysogen carrying the T7 RNA polymerase gene, preferably under the control of E. coli LAC promoter, is preferably used. To ensure maximum stability and plasmid viability, it is also preferred that no expression if the coding nucleic acid occur prior to induction. For this reason, an infectious agent (e.g., T7 or M13) is the most preferred method for the introduction of the RNA polymerase gene. This is because a plasmid cannot be introduced at will but must be present during growth. Further, it suffers from the same problem as the chromosomal copy in that it cannot be fully turned off. When the RNA polymerase is introduced by an infectious agents comprising a phage, for example T7, the endogenous promoter of the RNA polymerase is preferably used provided it is recognized by the prokaryotic host used. When the phage RNA polymerase is inserted into another infectious agent, such as M13, it is preferred that the promoter controlling the RNA polymerase expression comprise the heat-inducible λ promoter.

In practicing the invention, it is preferred that the expression of the coding nucleic acid occur during log phase growth of the host prokaryote. When the coding sequence uses a phage promoter, and the RNA polymerase is provided by an infectious agent which also includes the bacteriophage nucleic acid, it is preferred that the coding nucleic acid be transformed or transfected into the prokaryotic host. Then, the host is grown in a medium until log phase growth is obtained. The infectious agent is then added to the culture medium to provide the RNA polymerase necessary for expression of the coding nucleic acid and the bacteriophage nucleic acid which enhances the production of the toxic polypeptide.

When the bacteriophage nucleic acid and source of RNA polymerase are not contained on the same infectious agent, it is preferred that the coding nucleic acid and bacteriophage nucleic acid first be incorporated into the prokaryote host. Then, the thus transformed or transfected host is grown to log phase at which time the infectious agent encoding the required RNA polymerase is added to the culture medium.

In addition to the foregoing, if the required RNA polymerase is under control of a heat or otherwise inducible promoter, the conditions of the culture medium are changed, e.g., by raising the temperature or adding an inducing reagent, to facilitate expression of the RNA polymerase which enables expression of the coding nucleic acid.

The following is presented by way of example and is not to be construed as a limitation on the scope of the invention. Further, all references herein are expressly incorporated by reference.

EXAMPLE 1

Construction of Cloning Vector (pT7 SC) and Its Use for Expression of Yeast DNA Polymerase δ (POL3) in *Escherichia coli* Infected with Mutant Bacteriophage T7

This example describes a modification of a plasmid, pT7-7 (Tabor and Richardson (1985) *Proc. Natl. Acad. Sci. U.S.A.* 262:1074–1078) that allows expression of inserted genes from the phage T7 RNA polymerase promoter. The modification was designed to suppress read-through transcription from cryptic start sites on the plasmid in order to reduce expression in the absence of T7 RNA polymerase and thus improve the vector for use in the expression of highly toxic and/or readily degraded gene products. This vector (pT7SC) was used to stably clone the POL3 gene of *Saccharomyces cerevisiae*, which is unstable in all other cloning and expression vectors tested. Previously described expression strategies proved ineffective in overexpressing the POL3 gene product. A new strategy was developed which relies on infection by mutant bacteriophage T7 for induction. This system efficiently overproduced the POL3 gene product, DNA polymerase δ.

Three nuclear DNA polymerases—α, δ and ε have been characterized and shown to be encoded by essential genes in *Saccharomyces cerevisiae*. Previous work has shown that DNA polymerase δ was encoded by CDC2 (Sitney et al (1989) *Cell* 56:599–605; Boulet et al (1989) *EMBO J.* 8:1849–1854), which has since been renamed POL3. We and others have observed that POL3-containing plasmids are unstable in *E. coli* (Simon et al (1991) *EMBO J.* 10:2165–2170). Observations made while handling the gene suggested that uncontrolled expression is responsible for the instability, thus DNA polymerase δ must be toxic to *E. coli*. The goal of the present study was to develop a vector and expression strategy that allows stable cloning and expression of genes such as POL3 that are unstable in *E. coli* (Brosius (1984) *Gene* 27:161–172).

(a) Construction of a vector (pT7SC) which suppresses read-through transcription To stabilize the POL3 gene of *Saccharomyces cerevisiae* a new vector was developed. The promoter for β-lactamase and the rho-independent transcription terminators $T_1$ and $T_2$ from the rrnB operon of *E. coli* (Brosius (1984) *Gene* 27:161–172) were cloned into pT7-7 (Tabor and Richardson (1985) *Proc. Natl. Acad. Sci. U.S.A.* 262:1074–1078) upstream of the T7 promoter (FIG. 2).

Plasmid pKK223-3 (Pharmacia) was digested with HinDIII and Sca I. The 824 base fragment containing the β-lactamase gene upstream sequences and the rrnB terminators was purified from a low melting agarose gel by phenol extraction (Perbal (1984). A Practical Guide to Molecular Cloning. John Wiley & Sons, New York, N.Y.). The HindIII overhang was filled in with Klenow fragment to yield a blunt-ended molecule. Plasmid pT7-7 was cut with BglII and the overhangs were filled in. The 824 base fragment was then blunt-end ligated into pT7-7. Orientation was determined by cutting recombinants with DraI. Plasmid containing the properly oriented fragment was propagated and then digested with ClaI. The overhangs were filled in and the 824 base fragment was inserted by blunt-end ligation. Orientation was again checked by digestion with DraI.

The promoter was directed away from the cloning region and was followed downstream by the terminator sequences. The terminators occur in the inverted orientation from that found in vivo but are still functional, though with decreased efficiency, in this orientation (Brosius (1984) *Gene* 27:161–172). Some genes are so unstable in bacterial vectors that there is difficulty in obtaining DNA appropriate for further characterization, especially sequence analysis. In order to allow for the cloning of unstable genes with unknown sequence and orientation, the extra promoter and terminator elements were also inserted into the last restriction site of the pT7-7 polylinker, again such that the promoter is directed away from the cloning region. The completed plasmid is shown in FIG. 2 and has been named pT7SC (for stringent control).

(b) Cloning the POL3 gene

A map of the POL3 gene of *S. cerevisiae*, which encodes the catalytic subunit of DNA polymerase δ, is shown in FIG. 3A. This gene has an open reading frame of 3279 base pairs which is predicted to give rise to a protein of 124 kD (Boulet et al (1989) *EMBO J.* 8:1849–1854). Constructs of POL3 beginning at either the MluI site or the Nde I site and running to the carboxyl terminal HinD III site were unstable in expression vectors pT7-7, pET3C and pKK223-3. Constructs truncated to the BsmI site were stable in pT7-7 but protein was not observed upon induction. This restriction site occurs downstream from the putative exonuclease sequences in region IV (Wong et al (1989) *EMBO J.* 7:37–47; Simon et al (1991) *EMBO J.* 10:2165–2170) and this may have a bearing on both the stability of this construct and the lack of expressed protein.

The entire POL3 gene, however, was successfully and stably cloned into pT7SC as shown in FIG. 3B. The POL3 gene was obtained from a YCp50 construct between the SaLI and HindIII sites in which the upstream MluI site of POL3 was inserted at the vector SalI site such that each was regenerated (pBL304). Plasmid pBL304 was digested with SalI and HindIII and ligated into these same sites in pT7SC. The resultant recombinant was then cut with XbaI and MluI. The ends were filled in and the plasmid was recircularized. This construct (FIG. 3B) was used for expression.

Inappropriate expression is apparently suppressed by the presence of the promoters and terminator sequences, and the POL3 containing plasmid is stable in a variety of commonly used cell lines. Another gene which had previously proven difficult to work with due to instability, yeast HSP60, was also stabilized in this vector, suggesting that this vector is generally useful.

(c) Expression of POL3 by infection with mutant bacteriophage T7

The pT7SC vector relies on a T7 promoter for the expression of the POL3 gene, and therefore a cell line, BL21, that contains a chromosomal copy of the T7 RNA polymerase gene was used for expressing DNA polymerase δ.

The BL21 cell line carries the POL3 gene-containing plasmid without alteration, but the protein is not detected upon induction with IPTG (FIG. 4). A second approach was to use a protease deficient cell line and to provide the T7 RNA polymerase by infecting with mGP1-2 which is an M13 strain that contains the gene for T7 RNA polymerase under lac control. Again DNA polymerase δ was not detected upon infection and induction with IPTG (FIG. 4).

The protein encoded by gene 4 of bacteriophage T7 is toxic and very difficult to clone but is stable in *E. coli* during infection by T7 phage. Possible phage T7 activities involved in suppression of cellular functions include that of gene 2 protein, which binds to and inhibits *E. coli* RNA polymerase, and of gene 0.7, which encodes a protein kinase that also inactivates the host RNA polymerase. There are several genes in the "early region" of the genome that encode rather small proteins that have been detected upon infection but whose activities have not been characterized. These proteins may be peptide inhibitors of proteases or of other metabolic enzymes. A mutant phage that produces T7 RNA polymerase but that does not progress through its life cycle because of amber mutations in genes 3, 5 and 6 was also used. Genes 3 and 6 encode very potent endo and exonucleases which normally degrade the host DNA during an infection. Gene 5 encodes the catalytic subunit of T7 DNA polymerase, which is essential for replicating the phage genome. Upon infection with these mutant phage, effective overproduction of DNA polymerase δ was observed (FIG. 4). Only the lane containing cells harboring POL3 plasmid that have been infected with bacteriophage T7$_{356-}$ displays production of a 124 kD protein (arrow) corresponding to DNA polymerase δ, the POL3 product.

The foregoing experimental results were obtained using the following protocol. Fresh overnight cultures were diluted 100-fold in LB with 20 μg/ml ampicillin and incubated at 30° C. to an absorbance of 1. Induction was through either the addition of IPTG to 0.4 mM, infection with mGP1-2 at an MOI of 5 with addition of IPTG or by infection with bacteriophage T7$_{356-}$ at an MOI of 50. Incubations were then continued at 30° C. for 1 hour (T7 infection) or 3 hours (IPTG and mGP1-2 induction). A 1 ml aliquot was removed from each sample, the cells were pelleted and then resuspended in 80 μl of cracking buuer (60 mM Tris-HCl pH 6.8,1% mercaptoethanol, 10% glycerol, 3% SDS and 0.01% bromophenol blue). Half of this volume was loaded onto a 7.5% SDS-PA gel. *E. coli* RNA polymerase was run as molecular weight standard. The proteins were visualized by staining with Coomassie blue. The source of the T7 RNA polymerase is indicated above the lanes. Cells were either uninduced (−) or induced (+).

A time course of the expression of DNA polymerase δ is shown in FIG. 5. Cultures were grown and induced as described above with cell cracking and electrophoresis also the same. Aliquots were removed at the times after infection indicated above the lane. *E. coli* RNA polymerase was used as molecular weight standard.

Within several minutes of infection large amounts of DNA polymerase δ are detectable. The cells generally lyse between 150 and 180 minutes after infection. By way of comparison, when a wild-type T7 infects a culture, onset of lysis occurs within 15 to 20 minutes with total lysis occurring within approximately 45 minutes. The lysis observed in this example is believed to be due to effects produced by the toxic polypeptide on the integrity of the prokaryote's cell membrane.

These experiments have been repeated a number of times with all three systems and the results are invariant; DNA polymerase δ is not produced using the traditional systems but large amounts are obtained using infection by mutant phage.

(d) Expression of deleted and truncated constructs of DNA polymerase δ in *E. coli* infected with mutant bacteriophage T7

The full length construct (FIG. 6A) was digested with EcoRV and recirculated (FIG. 6B). The resulting plasmid would give rise to a 114 kD protein. A truncated form of POL3 (FIG. 56) was constructed by digesting both pBL304 and pT7SC with NdeI and HinDIII. The digests were then mixed for ligation. Recombinants were screened first by size and then by restriction mapping to identify the proper construct which should yield a 98 kD protein. A larger deletion (FIG. 6D) was constructed by digesting pT7sC/POL3 with Nco I and EcoRV. The ends were filled in and the plasmid was recirculated. This should give rise to a 78 kD protein.

The stable construct of the full length POL3 gene was cut at restriction sites flanking sequences predicted to encode exonuclease function and religated (FIGS. 6B and D). The first internal deletion, formed by EcoRV digestion, removes a 252 base segment which contains the exoI', exo I and exo II sequences. Site-specific mutations in these sequences in vivo resulted in the apparent reduction of proofreading activity of polymerase δ (Simon et al (1991) *EMBO J.* 10:2165–2170). Ligation regenerates a single EcoRV site which can be used to ensure the gene is in frame. The other internal deletion retains the first nine triplets at the amino terminus but removes the next 1212 bases to the second EcoRV site, combining the effects of the first deletion and the truncation.

The N-terminally truncated form of the gene was also cloned into the NdeI site of pT7SC as shown in FIG. 6C. The N-terminal truncation beginning at the NdeI site removes 660 bases from the amino terminus, while retaining all of the six conserved regions. This construct differs from the others in that the vector ribosome binding site and ATG spacing are retained (see position of XbaI and NdeI sites in FIG. 2).

An SDS-PA gel of expressions of these constructs is shown in FIG. 7. Expression was detected only for the full-length (124 kD) and truncated (98 kD) constructs. Both the full-length (124 kD) and truncated (98 kD) versions of the protein are overexpressed but the internal deletions (114 and 78 kD) do not give rise to protein upon induction. Site-specific mutants of POL3 affecting the deleted region showed DNA polymerase activity in vitro and complemented pol3 mutants (Simon et al (1991) *EMBO J.* 10:2165–2170).

However another study of site-specific mutants of the homologous regions in HSV Pol (Gibbs et al (1991) *Mol. and Cell. Biol.* 11:4786–4795) showed some mutants completely lacked polymerization activity. These authors suggested that the exonuclease region does not fold as a separate domain but interacts with the polymerase active site. If this is the case then deleting these regions may destabilize the protein and this is why expression from these constructs is not detected. In keeping with this interpretation, we showed above that a construct deleting the entire N-terminus through the exonuclease domain (BsmI site) could be stably cloned in any vector.

Although the strategies most commonly used for expression of genes in T7-based vectors were not effective in overexpressing the POL3 gene, we have demonstrated that infection with mutant bacteriophage T7 led to high levels of overexpression. We have obtained up to 15 mg of protein from as little as 3 grams of cells. The protein is not found in the soluble cell extract but is included and found in the insoluble material.

EXAMPLE 2

Construction of a New Cloning Vector (pT7Early) and Its Use to Identify the Bacteriophage T7 Sequences Which Stabilize Expression of Yeast DNA Polymerase δ (POL 3) in *E. coli*

The sequence of bacteriophage T7 has been deduced and the open reading frames (ORFs) have been identified. Dunn and Studier (1983) *J. Mol. Biol.* 166:477–535. Many ORFs correspond to genes of known function while others do not have defined functions. Many of the genes from 2.0 onward have known functions and, beginning with gene 2.5, are involved primarily in DNA replication. The functions involved in the enhancement of production of toxic proteins are probably expressed prior to the replication functions as some of these replication proteins are known to be toxic (i.e., gene 4 protein). Since the functions of interest are also probably toxic, it is necessary to clone the genes encoding them into a plasmid strictly controlling their expression. In order to clone and express the early region genes of T7 to test them for the ability to enhance DNA polymerase δ production, a vector compatible with pT7SC is modified to carry a T7 promoter flanked by termination sequences.

This vector (pT7 early) is constructed as follows. The SspI fragment from pT7SC which contains the rrnB termination sequences flanking the T7 promoter sequence and polylinker cloning region is gel purified. The ends are filled in by Klenow fragment and ClaI linkers are ligated to the ends. This fragment is then inserted into the ClaI site of PACYC 184 (Chang, A. C. Y. and Cohen, S. N. (1978) *J. Bacteriol.* 134:1141–1156). A fragment of T7 DNA containing genes 0.4 to 0.7 is obtained by digesting T7 DNA with NruI and gel purifying the 3269 base pair fragment. Gene 0.3 initially is not included because it encodes a protein that inhibits host restriction of phage DNA though this may not be its only function. Since the phage genes are carried on a plasmid grown in *E. coli* and many other common hosts that are restriction minus, restriction of the coding DNA is not a problem that must be overcome. The purified phage DNA fragment is then digested into two fragments with BstBI. The enzyme is removed by phenol extraction and the DNA recovered by ethanol precipitation. The ends of the fragments are filled in using Klenow fragment and PstI linkers are ligated to the ends. During removal of excess linkers by digestion with PstI, the unwanted sequences are multiply digested by DraI which does not cleave the fragment containing genes 0.4 to 0.7. This fragment is then cloned into the PstI site in the polylinker that has been inserted into pACYC184. This plasmid is used to transform a bacterial strain harboring the gene POL3 containing pT7SC. Induction is by infection with mGP1-2, which carries T7 gene 1 (RNA polymerase) under the control of the *E. coli* lac promoter, with the addition of IPTG.

A fragment containing T7 genes 1.1 through 2.0, which may also be involved in suppression of host function, is obtained by digesting T7 DNA with KpnI and gel purifying the 3575 base pair fragment. The ends are filled in with Klenow fragment and PstI linkers are added. This fragment is ligated into the PstI site of the modified pACYC184 vector which is tested as above. Alternatively, HindIII linkers can be added and this fragment inserted downstream of the fragment carrying the 0.4 to 0.7 genes, which provides for expression of all of these genes simultaneously.

Alternatively, the individual genes are isolated by using polymerase chain reaction amplification. These amplified genes are cloned into the above modified vector and tested for the ability to enhance production of DNA polymerase δ. The 0.3 gene is tested in this way to determine if it has a function other than inhibition of host restriction. This method is also used for constructing plasmids containing various combinations of the early region genes. The basis of the assay is the ability to overproduce DNA polymerase δ.

Having described the preferred embodiments of the present invention, it will appear to those of ordinary skill in the art that various modifications may be made to the disclosed embodiments, and that such modifications are intended to be within the scope of the invention as claimed.

All publications are expressly incorporated by reference to the same extent as if each individual publication or patent application was specifically and individually indicated to be incorporated by reference.

What is claimed is:

1. A prokaryotic host which expresses a toxic polypeptide, said host comprising:
    (a) a coding nucleic acid comprising a promoter operably linked to a nucleic acid coding for said toxic polypeptide; wherein said promoter is recognized by a RNA polymerase non endogenous to said prokaryotic host; and
    (b) a bacteriophage nucleic acid comprising at least one functional gene of an early region of a T7-like bacteriophage nucleic acid other than a gene encoding RNA polymerase, wherein said T7-like bacteriophage is selected from the group consisting of T1, T3, T7, ΦI, ΦII, BA14, A16, Φ1.2, K11, SP6, gh-1 and ΦCd1, and wherein said bacteriophage nucleic acid encodes a bacteriophage which is incapable of completing its life cycle; and
    c) a nucleic acid encoding said non-endogenous RNA polymerase;

wherein the level of production of said toxic polypeptide after induction in said prokaryotic host containing said nucleic acids is at least 50% greater than the level of production of said toxic polypeptide after induction in the same prokaryote containing only said coding nucleic acid.

2. The host of claim 1 wherein said T7-like bacteriophage nucleic acid is from a bacteriophage selected from the group consisting of T-3 and T-7.

3. A prokaryotic host which expresses a toxic polypeptide comprising:
    (a) a coding nucleic acid comprising an inducible promoter operably linked to a nucleic acid coding for said toxic polypeptide, and
    (b) a bacteriophage nucleic acid comprising at least one functional gene of an early region of a T7-like bacteriophage nucleic acid other than a gene encoding RNA polymerase, wherein said T7-like bacteriophage is selected from the group consisting of T3 and T7 and wherein said bacteriophage nucleic acid encodes a bacteriophage which is incapable of completing its life cycle, wherein the level of production of said toxic polypeptide after induction in said prokaryotic host containing coding and said bacteriophage nucleic acid is at least 50% greater than the level of production of said toxic polypeptide after induction in the same prokaryote containing only said coding nucleic acid.

4. The host of claim 2 or 3, wherein said prokaryote comprises *Escherichia coli*.

5. The host of claim 2 or 3 wherein said T7-like bacteriophage nucleic acid is from bacteriophage T7.

6. The host of claim 2 or 3 wherein said bacteriophage nucleic acid consists essentially of the early region of a T7 bacteriophage.

7. The host of claim 2 or 3 wherein said bacteriophage nucleic acid consists essentially of a mutant bacteriophage containing one or more mutant genes which permit early region gene expression but which prevent said mutant bacteriophage from completing its life cycle.

8. The host of claim 2 or 3 wherein said coding nucleic acid and said bacteriophage nucleic acid are contained on different plasmids.

9. The host of claim 2 or 3 wherein said coding nucleic acid and said bacteriophage nucleic acid are contained on the same plasmid.

10. The host of claim 2 wherein said promoter comprises a promoter recognized by a T3 or T7 bacteriophage RNA polymerase and said nucleic acid encoding said RNA polymerase encodes said T3 or T7 bacteriophage RNA polymerase.

11. The host of claim 2 or 3 wherein said prokaryote comprises a member of the genera Escherichia.

12. The host of claim 2 or 3 wherein said prokaryote comprises *Escherichia coli* having lon protease activity.

13. The host of claim 2 or 3 wherein said bacteriophage nucleic acid consists essentially of a nucleic acid containing genes 0.4 to 0.7 of T7 bacteriophage.

14. The host of claim 2 or 3 wherein no toxic polypeptide is produced in a prokaryote containing only said coding nucleic acid.

15. The host of claim 2 or 3 wherein said bacteriophage nucleic acid consists essentially of a nucleic acid containing genes 0.3 through 2.0 of T7 bacteriophage.

16. A prokaryotic host which expresses a toxic polypeptide comprising:
    (a) a coding nucleic acid coding for said toxic polypeptide; and
    (b) a bacteriophage nucleic acid consisting essentially of the early region of a T7 bacteriophage,
wherein the level of production of said toxic polypeptide after induction in said prokaryotic host containing coding and said bacteriophage nucleic acid is at least 50% greater than the level of production of said toxic polypeptide after induction in the same prokaryote containing only said coding nucleic acid.

17. A host according to claim 10 wherein said T7-like bacteriophage RNA polymerase is selected from the group consisting of T-3 and T-7 bacteriophage RNA polymerases.

18. A host according to claim 17 wherein said T7-like bacteriophage RNA polymerase is T7 bacteriophage RNA polymerase.

19. A prokaryotic host which expresses a toxic polypeptide comprising:
    (a) a coding nucleic acid coding for said toxic polypeptide; and
    (b) a bacteriophage nucleic acid comprising all early region genes of a T3 or T7 bacteriophage except for gene 1 encoding a RNA polymerase for which inclusion is optional, wherein said bacteriophage nucleic acid is mutated at least in one gene selected from the group consisting of genes 3, 5 and 6 such to be incapable of completing its life cycle,
wherein the level of production of said toxic polypeptide after induction in said prokaryotic host containing coding and said bacteriophage nucleic acid is at least 50% greater than the level of production of said toxic polypeptide after induction in the same prokaryote containing only said coding nucleic acid.

20. The host of claim 19 wherein the host is *Eschericia coli.*

21. The host of claim 19 wherein the bacteriophage is T7.

22. The host of claim 2 or 3 wherein said bacteriophage nucleic acid consists essentially of a nucleic acid containing genes 0.7 through 2.0 of T7 bacteriophage.

23. A prokaryotic host which expresses a toxic polypeptide comprising:
    (a) a coding nucleic acid comprising an inducible promoter operably linked to a nucleic acid coding for said toxic polypeptide; and
    (b) a bacteriophage nucleic acid comprising at least one functional gene of an early region of a T7 bacteriophage nucleic acid other than a gene encoding RNA polymerase, wherein said bacteriophage nucleic acid encodes a bacteriophage which is incapable of completing its life cycle,
wherein the level of production of said toxic polypeptide after induction in said prokaryotic host containing coding and said bacteriophage nucleic acid is at least 50% greater than the level of production of said toxic polypeptide after induction in the same prokaryote containing only said coding nucleic acid.

24. A method for producing a polypeptide in a prokaryotic host, said method comprising
    (a) forming a prokaryotic host comprising
        (i) a coding nucleic acid comprising an inducible promoter operably linked to a nucleic acid coding for a toxic polypeptide;
        (ii) a bacteriophage nucleic acid comprising at least one functional gene of an early region of a T7-like bacteriophage nucleic acid other than a gene encoding RNA polymerase, wherein said T7-like bacteriophage is selected from the group consisting of T1, T3, T7, ΦI, ΦII, BA14, A16, Φ1.2, K11, SP6, gh-1 and ΦCd1, and wherein said bacteriophage, nucleic acid encodes a bacteriophage which is incapable of completing its life cycle, and
    (b) subjecting said host to conditions which permit the expression of said coding nucleic acid,
wherein the level of production of said toxic polypeptide after induction in said prokaryotic host containing said coding and said bacteriophage nucleic acid is at least 50% greater than the level of production of said toxic polypeptide after induction in the same prokaryote containing only said coding nucleic acid.

25. The method of claim 24 wherein said T7-like bacteriophage nucleic acid is from a bacteriophage.

26. A method for producing a polypeptide in a prokaryotic host, said method comprising
    (a) forming a prokaryotic host comprising a coding nucleic acid comprising a promoter operably linked to a nucleic acid coding for a toxic polypeptide, wherein said promoter is recognized by a RNA polymerase non-endogenous to said prokaryotic host; and
    (b) infecting said prokaryotic host with
        i) a bacteriophage nucleic acid comprising at least one functional gene of an early region of a T7-like bacteriophage nucleic; acid other than a gene encoding RNA polymerase, wherein said T7-like bacteriophage is selected from the group consisting of T3 and T7, and wherein said bacteriophage nucleic acid encodes a bacteriophage which is incapable of completing its life cycle; and
        ii) a nucleic acid encoding said RNA polymerase non-endogenous to said prokaryotic host;

wherein said infection permits the expression of said coding nucleic acid, wherein the level of production of said toxic polypeptide after induction in said prokaryotic host containing coding and said bacteriophage nucleic acid is at least 50% greater than the level of production of said toxic polypeptide after induction in the same prokaryote containing only said coding nucleic acid.

27. The method of claim 25 or 26 wherein said prokaryotic host is selected from the group consisting of members of the genera Escherichia.

28. The method of claim 25 or 26 wherein said prokaryotic host is *Escherichia coli.*

29. The method of claim 25 or 26 wherein said T7-like bacteriophage nucleic acid is from a bacteriophage T7.

30. The method of claim 25 or 26 wherein said bacteriophage nucleic acid consists essentially of the early region of a T7 bacteriophage.

31. The method of claim 25 or 26 wherein said bacteriophage nucleic acid consists essentially of a mutant bacteriophage containing one or more mutant genes which permit early region gene expression but which prevent said mutant bacteriophage from completing its life cycle.

32. The method of claim 25 or 26 wherein said bacteriophage nucleic acid consists essentially of a nucleic acid containing genes 0.4 to 0.7 of T7 bacteriophage.

33. The method of claim 25 wherein no toxic polypeptide is produced in a prokaryote containing only said coding nucleic acid.

34. The method of claim 26 wherein no toxic polypeptide is produced in a prokaryote containing only said coding nucleic acid.

35. The method of claim 25 or 26 wherein said bacteriophage nucleic acid consists essentially of a nucleic acid containing genes 0.3 through 2.0 of T7bacteriophage.

36. The method of claim 25 or 26 wherein said bacteriophage nucleic acid consists essentially of a nucleic acid containing genes 0.7 through 2.0 of T7 bacteriophage.

37. A method for producing a polypeptide in a prokaryotic host, said method comprising (a) forming a prokaryotic host comprising
   (i) a coding nucleic acid comprising an inducible promoter operably linked to a nucleic acid coding for a toxic polypeptide;
   (ii) a bacteriophage nucleic acid comprising at least one functional gene of an early region of a T7 bacteriophage nucleic acid other than a gene encoding RNA polymerase, wherein said bacteriophage nucleic acid encodes a bacteriophage which is incapable of completing its life cycle, and (b) subjecting said host to conditions which permit the expression of said coding nucleic acid, wherein the level of production of said toxic polypeptide after induction said prokaryotic host containing said coding and said bacteriophage nucleic acid is at least 50% greater than the level of production of said toxic polypeptide after induction in the same prokaryote containing only said coding nucleic acid.

* * * * *

UNITED STATES PATENT AND TRADEMARK OFFICE
CERTIFICATE OF CORRECTION

PATENT NO. : 5,843,703
DATED : December 1, 1998
INVENTOR(S) : CAMPBELL et al.

It is certified that error appears in the above-identified patent and that said Letters Patent is hereby corrected as shown below:

Column 6, line 12, delete "sing" and insert therefore --using--.

Column 7, line 20, delete "Polymerase 6" and insert therefore --Polymerase δ--.

Column 11, line 31, delete "PACYC" and insert therefore --pACYC--.

Column 12, line 18, delete "Aprokaryotic" and insert therefore --A prokaryotic--.

Column 12, line 23, delete "non endogenous" and insert therefore --non-endogenous--.

Column 14, line 48, delete "is from a bacteriophage." and insert therefore --is from a T3 or T7 bacteriophage.--.

Signed and Sealed this

Twenty-third Day of March, 1999

Attest:

Q. TODD DICKINSON

*Attesting Officer*   Acting Commissioner of Patents and Trademarks